United States Patent [19]

Marchin et al.

[11] Patent Number: 5,366,636
[45] Date of Patent: Nov. 22, 1994

[54] METHOD OF TREATING WATER WITH RESIN BOUND IONIC SILVER

[75] Inventors: George L. Marchin; Jack L. Lambert, both of Manhattan, Kans.

[73] Assignee: Kansas State University Research Foundation, Manhattan, Kans.

[21] Appl. No.: 210,876

[22] Filed: Mar. 18, 1994

[51] Int. Cl.$^5$ ............... B01D 15/00; C07C 51/42; B01J 39/00
[52] U.S. Cl. ................... 210/665; 210/683; 210/764
[58] Field of Search ............ 210/665, 683, 764

[56] References Cited

U.S. PATENT DOCUMENTS

| | | |
|---|---|---|
| 2,434,190 | 1/1948 | Barnes et al. |
| 2,692,855 | 10/1954 | Juda |
| 3,382,039 | 5/1968 | Calmon et al. |
| 3,817,860 | 6/1974 | Lambert et al. |
| 4,187,183 | 2/1980 | Hatch |
| 4,190,529 | 2/1980 | Hatch |
| 4,238,477 | 12/1980 | Lambert et al. |
| 4,358,546 | 11/1982 | Naomi et al. |
| 4,895,905 | 1/1990 | Schneider et al. |
| 4,999,190 | 3/1991 | Fina et al. ................ 424/670 |
| 5,093,078 | 3/1992 | Hollis et al. ............. 210/754 |
| 5,139,981 | 8/1992 | Kurland |
| 5,220,058 | 6/1993 | Fish et al. ................ 210/683 |

FOREIGN PATENT DOCUMENTS

| | | |
|---|---|---|
| 122647 | 10/1946 | Australia. |
| 576969 | 4/1946 | United Kingdom. |
| 1195242 | 6/1970 | United Kingdom ........ 210/665 |

OTHER PUBLICATIONS

Jay Montemarano, "Demand Release Polyiodide Disinfectants", Water Technology, Aug. 1990, pp. 65–66.

Primary Examiner—Neil McCarthy
Attorney, Agent, or Firm—Tilton, Fallon, Lungmus & Chestnut

[57] ABSTRACT

A method is provided for treating drinking water for disinfecting and/or removing iodide. The method utilizes resin bound silver ions. For performing the disinfection or iodide removal with minimal release of silver ions into the water being treated, a chelating resin having iminodiacetic acid chelating groups is employed, and the resin is loaded with not over 0.5 mol of silver ion per mol of iminodiacetate.

5 Claims, No Drawings

METHOD OF TREATING WATER WITH RESIN BOUND IONIC SILVER

FIELD OF INVENTION

The field of this invention is the treatment of water with silver to disinfect the water and/or remove halide therefrom. The invention is particularly concerned with the treatment of drinking water to remove iodide.

BACKGROUND OF INVENTION

It is known that metallic silver can be an effective bactericide for treating water. For this purpose U.S. Pat. No. 2,434,190 describes the preparation of a "silvered" anion exchange resin. As described in this patent, the anion exchange resin in the sodium form may be treated with a solution of silver nitrate to load the resin with silver ions. The resin is next treated with a reducing agent such as potassium metabisulfite to form metallic silver. It is stated that the silvered resin can be used for disinfecting water.

U.S. Pat. No. 2,692,855 discloses using a cation exchange resin in a silver ion form for disinfection of water. As described in the patent, for example, a cation exchange resin in the hydrogen form may be treated with a solution of a silver salt to exchange silver ions for hydrogen ions, thereby producing a resin for disinfecting water. However, the presence of silver ions in drinking water can be a health hazard, and drinking water contains metal ions that will exchange with the silver ions on the resin. To minimize release of silver ions into the solution being treated, the water can first be demineralized by passing it through an cation exchange resin in the hydrogen form to remove metal cations.

Cation exchangers, such as zeolite and synthetic cation exchange resins, have been reacted with solutions of silver salts to exchange the silver ion for the hydrogen or alkali metal cations of the exchangers. Such silver ion-containing resins have been used to remove halides from water, such as the removal of chloride ions from sea water. See U.S. Pat. No. 3,382,039, United Kingdom Patent 576,969 and Australian Patent 122,647. Silver ion-containing cation exchange resins have also been proposed for use in removing iodine and methyl iodide from waste streams, and removing halides from liquid carboxylic acid (U.S. Pat. No. 5,139,981). In such applications, the release of silver ions into the solution being processed may not be as objectionable as with potable water.

SUMMARY OF INVENTION

Prior art methods of using silver ion-containing zeolites and synthetic cation exchange resins to treat drinking water have the disadvantage of releasing silver ions into the treated water. Drinking water contains cations such as calcium, magnesium, and sodium which tend to exchange with the silver ions in the zeolite or resin. For health reasons, it is desired to avoid excessive amounts of silver ions in drinking water. For example, United States Environmental Protection Agency established as a safety standard that drinking water should contain less than 50 $\mu$g of silver per liter of water. In treating drinking water to disinfect the water and/or to remove iodide therefrom it is therefore important to carry out the treatment with minimized release of silver ions.

The present invention utilizes a novel resin composition which comprises a chelating resin containing iminodiacetate acid groups at the metal chelating sites, which provide paired acetate groups and a tertiary amine for chelating action. The resin composition is further characterized by containing diacetate-chelated silver ions in a ratio of not over 1 silver ion per two iminodiacetate groups. The resin is thereby loaded with silver ions to not over 50% of resin capacity. The silver ions are thereby retained within the resin beads while effectively killing microorganisms, and/or removing iodide from the water. The resulting resin beads tenaciously retain the silver ions and resists their elution by the cations normally found in water, such as hydrogen, sodium, calcium, and magnesium ions.

The method of this invention also utilizes the retaining capacity of the silver chelating resin composition to minimize the release of silver iodide, silver chloride, or other silver halide into the drinking water. Although the exact mechanism of retention is not fully understood, it has been found that the soluble silver iodide or other silver halide formed within the resin granules or beads are retained therein, resulting in the production of drinking water with minimal content of iodide, silver ion, or silver iodide.

The method of this invention can be used as a desirable secondary treatment for drinking water which has been contacted with porous granules of a polyiodide anion exchange resin to disinfect the water. Such treatment may release iodide ions into the drinking water. In one preferred embodiment, the drinking water has initially been disinfected by being contacted with an anion exchange resin containing pentaiodide ($I_5^-$) ions.

DETAILED DESCRIPTION

For preparing the silver ion containing chelating resin composition, a resin containing iminodiacetate groups is used. Bio-Rad Laboratories, Richmond, Calif. sells such chelating resins which are polystyrene divinyl benzene copolymers containing iminodiacetate functional groups. These resins are identified as "Chelex 20" (macroporous form) and "Chelex 100" (gel form). Either the gel or macroporous form can be used, but the gel form Chelex resin is preferred. Chelex 100 is available in analytical and biotechnology grades both of which are suitable for use in this invention. Chelex 20 is a technical grade resin which can also be used.

The described chelating resin is contacted with an aqueous solution of a silver salt, such as the nitrate, perchlorate, or acetate salts. The silver ions are removed from the solution and immobilized by the paired chelating groups. This conversion to a silver form should be carried out in relation to the stated cation capacity of the resin, viz. in milliequivalents per milliliter. The resin composition is prepared so that it does not contain silver ion which is easily exchanged and/or eluted. The quantity of silver ions applied to the chelating resin should not exceed one silver ion per two iminodiacetate groups, which corresponds to a 50% or less capacity loading. Stated otherwise, the prepared resin composition should contain not over 0.5 mol of silver per mol of iminodiacetate. Resin compositions can also be used which contain less the stated maximums of silver, such as 0.3 to 0.5 mol of silver per mol of iminodiacetate.

Preparation of Silver-Chelex 100 Resin

Approximately 300 milliequivalents of Chelex 100, a gel-type chelating resin (50–100 mesh or 100–200 mesh, sodium form; Bio-Rad Laboratories, Richmond, Calif.) is suspended in an excess of distilled water. The settled wet capacity of this resin is 0.40 meq/ml. This resin contains iminodiacetate chelating groups. Total volume is approximately 750 ml of settled bed volume. The pH of the aqueous suspension is measured with a standard glass electrode and adjusted with 1.0N NaOH to at least pH 8.0 if required. Most commercial lots of the resin will generate a suspension with pH>8.0 but an occasional lot may require standardization. It is believed important to open up both of the acetate groups on the iminodiacetate to accept the silver cation, $Ag^+$.

A solution of silver nitrate ($AgNO_3$) 150 milliequivalents (25.48 grams) in 200 ml distilled water is added to the suspended Chelex 100. The mixture is stirred with an overhead glass stirring rod to prevent bead fracture. After one hour the stirrer is turned off and the gel allowed to settle. The bed volume typically shrinks to 500 ml due to neutralization of the electrorepulsive effects of the adjacent diacetate groups.

The supernatant solution is tested with 0.10M KI solution and produces no silver iodide precipitate. The free silver ion concentration of the supernatant solution is undetectable with a silver select ion electrode ($Ag^+ < 1 \times 10^{-6}M$). If more than 0.5 equivalent $Ag^+$:equivalent Chelex resin is used in preparation an extensive washing procedure is required to eliminate the free silver ion in aqueous washes.

Preparation of Silver-Chelex 20 Resin

Approximately 300 milliequivalents of Chelex 20, a macroporous chelating resin (20–50 mesh, sodium form; Bio-Rad Laboratories, Richmond, Calif.) is suspended in an excess of distilled water. This resin contains iminodiacetic acid-type chelating groups. Total volume is approximately 500 ml of settled bed volume. (This resin requires only 500 ml to provide 300 meq of binding capacity.) The pH of the aqueous suspension is measured with a standard glass electrode and adjusted with 1.0N NaOH to at least pH 8.0 if required. Most commercially available lots of the resin will generate a suspension with pH >8.0 but the occasional lot requires standardization. This is important to open up both of the acetate groups on the iminodiacetate to accept the silver cation, $Ag^+$.

A solution of silver nitrate ($AgNO_3$) 150 milliequivalents (25.48 grams) in 200 ml distilled water is added to the suspended Chelex 20. The mixture is stirred with an overhead glass stirring rod to prevent bead fracture. After one hour the stirrer is turned off and the gel allowed to settle. The bed volume typically shrinks to 450 ml which is probably due to neutralization of the electrorepulsive effects of the adjacent diacetate groups.

The supernatant solution is tested with 0.10M KI solution and produces no silver iodide precipitate. The free silver ion concentration of the supernatant solution is undetectable with a silver-selective ion electrode ($Ag^+ < 1 \times 10^{-6}M$). If more than 0.5 equivalent $Ag^+$:equivalent Chelex resin is used in preparation an extensive washing procedure is required to eliminate the free silver ion in aqueous washes.

An experimental investigation was conducted with the resins prepared as described above.

First Experiment

*Escherichia coli* B, strain NP 4, was grown overnight in Benzer Broth (9.0 gm Bacto Tryptone [Difco] and 5.0 gm NaCl per liter) in a shaking water bath (New Brunswick) at 37° C. Organisms were centrifuged at $10,000 \times g$ for 5 minutes in a Beckman J-21 centrifuge at 4° C., resuspended in deionized water, washed, centrifuged and diluted 1:100 in deionized water to give approximately $1 \times 10^7$ colony forming units per ml (cfu/ml). These organisms were allowed to flow through beds of the silver resins.

Samples of the water were plated on nutrient agar plates (Benzer Broth solidified with 15 gm Bacto Agar [Difco] per liter); 0.10 ml samples were spread with a sterile glass rod. Platings were done in triplicate. As a control the input culture was appropriately diluted ($10^{-5}$) and also plated in triplicate as described above. Plates were incubated for 16 hrs. at 37° and colony forming units determined. Data are expressed in the following table.

Bacterial Concentration *E. Coli* (CFU/ML)

| Trial | Input | Output |
| --- | --- | --- |
| Silver-CHELEX 20 Resin | $2.79 \times 10^7$ | 0 |
| Silver-CHELEX 100 Resin | $2.79 \times 10^7$ | 0 |

This data illustrates the bactericidal activity of the silver resin compounds. The data is surprising in light of the tenacity with which the silver ion are held by the iminodiacetate resin. Further, tests of the resin eluates with a solution of $1 \times 10^{-1}M$ KI formed no visible precipitate, indicated no significant elution of the silver ion, $Ag^+$.

Second Experiment

An aqueous solution of potassium iodide (KI) $1 \times 10^{-5}M$ which contains 1.27 mg per liter of iodide anion ($I^-$) was passed under gravity flow through a small 5 ml column of the three silver ion-containing resin materials prepared as described above. The iodide anion concentration was determined using an iodide-selective electrode to record the electrode potential. The electrode potential was converted to iodide concentration by reference to a standard curve. The results of four trials are reported in the following table.

| | Iodide ($I^-$) Removal by Silver Resins | | | |
| --- | --- | --- | --- | --- |
| Trial | Input millivolts | Solution ppm (mg/l) $I^-$ | Output millivolts | Solution ppm (mg/l) $I^-$ |
| Ag-Chelex 20 | +120 | 1.27 | +490 | <.00127 |
| Ag-Chelex 100 | +120 | 1.27 | +545 | <.00127 |

In both trials the iodide anion concentration in the eluates was less than the lowest concentration that could be detected with the iodide-selective electrode (220 millivolts: 0.00127 ppm).

Preferred Combination Treatment

In a preferred application of the method of this invention, the water to be treated is first passed through a quaternary ammonium exchange resin, which as first used has more than sixty-five percent of the ion exchange sites therein associated with pentaiodide ion ($I_5^-$). For example, a resin of this kind can be prepared as described in the example of U.S. Pat. No. 4,999,190. The resulting resin will have about ninety-seven percent of its total sites iodinated and about seventy percent of the sites will be $I_5^-$ sites. The water to be disinfected is first passed through a bed containing granules of this resin. Bacteria and other microorganisms will be killed and the treated water will contain iodide ions (I−). To assure complete disinfection and to remove the iodide ions, the initially treated water is passed through one of the silver ion-containing resins prepared as described above. The combined treatment will produce bacterially sterile water substantially free of iodide and silver ions. To assure that the treated water complies with the EPA standard of 50 μg silver/1, activated charcoal may be mixed with the silver chelating resin or used as a tertiary treatment.

Comparative Example

Silver Chelex 20

Silver Chelex 20 and 100 resins were prepared as described above containing 0.5 mol of silver ion per mol of iminodiacetate. A sulfonic acid resin was loaded with silver ions to 50% capacity and three zeolite exchangers were loaded at less than their maximum capacities. The preparation procedure is described below.

Preparation of Silver Sulfonic Acid Resin

Approximately 300 milliequivalents of AG 50W-XS, a strong cation exchange resin (20–100 mesh, hydrogen form; Bio-Rad Laboratories, Richmond, Calif.) is suspended in an excess of distilled water. Total volume is approximately 500 ml of settled bed volume.

A solution of silver nitrate ($AgNO_3$) 150 milliequivalents (25.48 grams) in 200 ml distilled water is added to the suspended AG 50W-X8 resin. (This corresponded to 0.5 mol silver per mol sulfonate.) The mixture is stirred with an overhead glass stirring rod to prevent bead fracture. After one hour the stirrer is turned off and the gel allowed to settle.

Preparation of Silver Zeolites

Zeolite cation exchange material (Fisher Chemical Company) was utilized in three commercially available forms which are marketed as molecular sieves; Type 5A, in 1/16 inch pellets; Grade 512, in 4–8 mesh beads; and Grade 513, in 4–8 mesh beads. These zeolites were composed of alumina silicate with either sodium or calcium cations.

The three zeolites were "converted" to the silver cation form by suspending 100 cm$^3$ of each material in 100 ml of 0.10M silver nitrate ($AgNO_3$) solution for 24 hr. at room temperature. The total volume of each of the silver nitrate-zeolite preparations was in excess of 150 ml. After overnight reaction some darkening of the solution occurred. After 24 hr. the excess $AgNO_3$ was decanted and the zeolite washed three times with borosilicate-glass distilled water.

Column Experiments

All six materials (two Chelexes, the silver sulfonic acid resin and three zeolites) were individually placed into 20 ml syringes with fiber glass plugs. Distilled water, Manhattan, Kans., city tap water (approximately 300 ppm total dissolved solids), or tapwater spiked with $1 \times 10^{-5}$M KI was allowed to flow through the resin beds. This concentration of KI was chosen because it is a typical concentration of iodide anion that is encountered when polyiodide anion exchange resins (triiodide or pentaiodide) are used in the chemical disinfection of water. Column eluates were then tested for free silver or iodide ions ($Ag^+$ or $I^-$) using appropriate ion selective electrodes and reference to a standard Nernst equation relating a millivolt reading to the respective ion concentration.

The results of these tests are summarized below in Tables 1 and 2.

Table 1. Free silver ion concentrations of eluates from small columns of silver resins using distilled water.

| RESIN MATERIALS | $[Ag^+]$ M |
| --- | --- |
| Ag-Chelex 20, 100 | $0.9 \times 10^{-5}$ |
| Ag-Sulfonic Acid | $1.3 \times 10^{-3}$ |
| Ag-Zeolite 5A | $1.1 \times 10^{-2}$ |
| Ag-Zeolite 512 | $1.7 \times 10^{-2}$ |
| Ag-Zeolite 513 | $1.6 \times 10^{-2}$ |

Table 2. Free silver ion concentrations of eulates from small columns of silver resins using tap water containing $1 \times 10^{-5}$M KI ( 120 mVolts).

| RESIN MATERIALS | $[Ag^+]$ M |
| --- | --- |
| Ag-Chelex 20, 100 | $<1.0 \times 10^{-6}$ |
| Ag-Sulfonic Acid | $1.2 \times 10^{-3}$ |
| Ag-Zeolite 5A | $1.1 \times 10^{-2}$ |
| Ag-Zeolite 512 | $1.7 \times 10^{-2}$ |
| Ag-Zeolite 513 | $1.6 \times 10^{-2}$ |

All resin materials removed the iodide, reducing I−mol concentration to below $1.0 \times 10^{-7}$. The important difference was that the sulfonate and zeolites released much more silver ion into the water than did the Chelex 20 and/or resins. The difference was several orders of magnitude.

We claim:

1. A method of treating drinking water for disinfecting and/or removing iodide, comprising contacting the drinking water with porous granules of a chelating resin having iminodiacetate acid chelating groups bonded to silver ions, said resin containing not over 0.5 mol of silver ion per mol of iminodiacetate, and separating the treated water from the granules.

2. The method of claim 1 in which the drinking water contains iodide ions which are removed therefrom by said contacting.

3. The method of claim 1 in which the water contains microorganism that are killed by said contacting.

4. The method of any one of claims 1, 2 or 3 in which said chelating resin is a gel-type resin.

5. The method of treating drinking water to kill microorganisms therein in which the water to be disinfected is initially contacted with porous granules of a polyiodide anion exchange resin resulting in the release of iodide ions into the treated water, wherein the improvement comprises contacting the treated iodide-containing water with porous granules of a chelating resin, said granules containing bound silver ions which react with the iodide ions to form substantially insoluble silver iodide, said chelating resin having iminodiacetate acid chelating groups and containing not over 0.5 mol of silver ion per mol of iminodiacetate.

* * * * *